(12) United States Patent
Mourelle Mancini et al.

(10) Patent No.: US 12,396,932 B2
(45) Date of Patent: Aug. 26, 2025

(54) GOLD AND PALMITOYL PENTAPEPTIDE-4 NANOPARTICLES

(71) Applicant: INFINITEC ACTIVOS, S.L., Barcelona (ES)

(72) Inventors: Marisabel Mourelle Mancini, Barcelona (ES); Maria Elisa Alea Reyes, Barcelona (ES)

(73) Assignee: INFINITEC ACTIVOS, S.L., Barcelona (ES)

( * ) Notice: Subject to any disclaimer, the term of this patent is extended or adjusted under 35 U.S.C. 154(b) by 16 days.

(21) Appl. No.: 18/311,704

(22) Filed: May 3, 2023

(65) Prior Publication Data

US 2023/0270636 A1      Aug. 31, 2023

Related U.S. Application Data

(63) Continuation of application No. 17/042,500, filed as application No. PCT/EP2019/057695 on Mar. 27, 2019, now abandoned.

(30) Foreign Application Priority Data

Mar. 28, 2018 (ES) .............................. ES201830311

(51) Int. Cl.
*A61K 8/19* (2006.01)
*A61K 8/64* (2006.01)
*A61Q 19/08* (2006.01)

(52) U.S. Cl.
CPC .................. *A61K 8/19* (2013.01); *A61K 8/64* (2013.01); *A61Q 19/08* (2013.01); *A61K 2800/412* (2013.01); *A61K 2800/413* (2013.01); *A61K 2800/654* (2013.01)

(58) Field of Classification Search
CPC . A61Q 19/08; B82Y 5/00; A61K 8/19; A61K 8/64; A61K 2800/412; A61K 2800/413; A61K 2800/654; A61K 8/65; A61K 9/51
See application file for complete search history.

(56) References Cited

U.S. PATENT DOCUMENTS

2009/0136595 A1    5/2009    Shah et al.

FOREIGN PATENT DOCUMENTS

| EP | 2228393 A1 | 9/2010 |
| FR | 2783169 A1 | 3/2000 |
| WO | 0015188 A1 | 3/2000 |
| WO | 2008079898 A1 | 7/2008 |
| WO | 2008140594 A2 | 11/2008 |
| WO | 2012173312 A1 | 12/2012 |

OTHER PUBLICATIONS

Biancamaria Baroli, "Penetration of Nanoparticles and Nanomaterials in the Skin: Fiction or Reality?", Journal of Pharmaceutical Sciences, vol. 99, No. 1, pp. 21-50, 2010.

(Continued)

*Primary Examiner* — Marianne C Seidel
*Assistant Examiner* — Amanda Michelle Petritsch
(74) *Attorney, Agent, or Firm* — Sughrue Mion, PLLC

(57) ABSTRACT

A gold nanoparticles conjugated with palmitoyl pentapeptide-4 (Palm-L-Lys-L-Thr-L-Thr-L-Lys-L-Ser-OH), compositions comprising them, use thereof in cosmetic treatments, as well as methods for obtaining the nanoparticles.

13 Claims, 1 Drawing Sheet

Specification includes a Sequence Listing.

(56) References Cited

OTHER PUBLICATIONS

Rakesh Gupta, et al., "Penetration of Gold Nanoparticles Through Human Skin: Unraveling Its Mechanisms at the Molecular Scale", The Journal of Physical Chemistry B, vol. 120, No. 29, pp. 7133-7142, 2016.
Rakesh Gupta, et al., "Effect of Size and Surface Charge of Gold Nanoparticles on Their Skin Permeability: a Molecular Dynamics Study", Scientific Reports, vol. 7, No. 45292, pp. 1-13, 2017.
International Search Report and Written Opinion for Corresponding International Application No. PCT/EP2019/057695 (11 Pages) (Jun. 11, 2019).

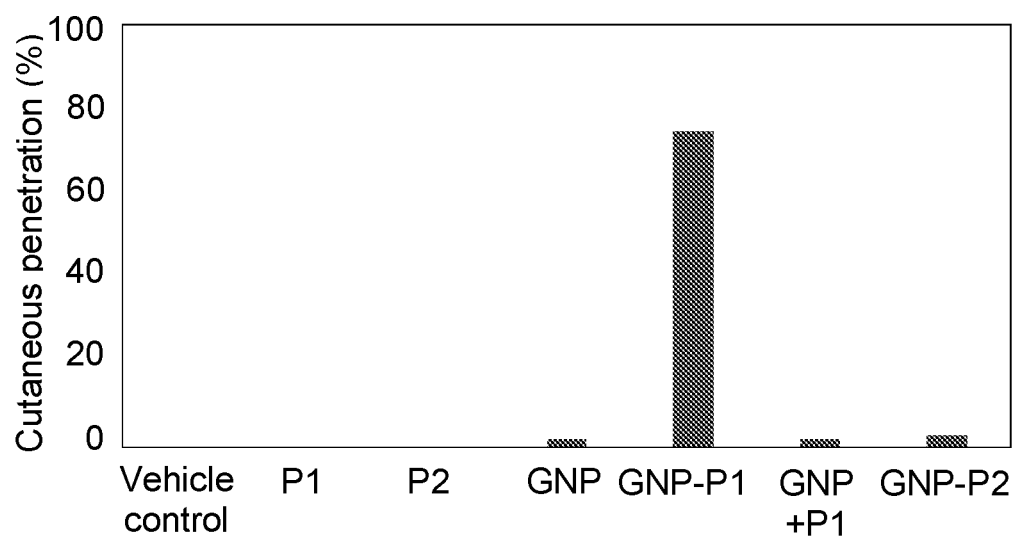

GOLD AND PALMITOYL PENTAPEPTIDE-4 NANOPARTICLES

CROSS-REFERENCE TO RELATED APPLICATIONS

This application is a continuation of U.S. patent application Ser. No. 17/042,500, filed Sep. 28, 2020, which in turn is a 371 of PCT/EP2019/057695, filed Mar. 27, 2019, which claims the benefit of Spanish Patent Application No. P201830311, filed Mar. 28, 2018, the contents of each of which are incorporated herein by reference.

REFERENCE TO A SEQUENCE LISTING SUBMITTED ELECTRONICALLY VIA EFS-WEB

The content of the electronically submitted sequence listing, file name: 20ABG-1046-C.xml; size: 3 kilobytes; and date of creation: May 3, 2023, filed herewith, is incorporated herein by reference in its entirety.

FIELD OF THE INVENTION

The present invention relates to palmitoyl pentapeptide-4 conjugated gold nanoparticles, compositions comprising them, use thereof in cosmetic treatments, as well as methods for obtaining said nanoparticles.

BACKGROUND OF THE INVENTION

The first noticeable sign of skin aging is the formation of fine lines and wrinkles. These fine lines appear in different facial areas and are the most easily recognized signs of aging. Fine lines are the first to appear. These small, somewhat shallow wrinkles tend to be noticed in the outer corners of the eyes. They are also known as laugh lines or crow's feet. Fine lines can also be located on the cheeks. On the forehead, wrinkles are noticed as horizontal lines and may be brought out by facial expressions, and they tend to become deeper over time. Smaller sized vertical lines between the eyebrows are caused by furrowing the brow.

There are a number of cosmetic products on the market to improve the appearance of the skin with respect to aging, particularly with respect to wrinkles.

The topical administration of cosmetic or therapeutic agents is a challenge in the field of cosmetic or pharmaceutical formulations since the skin has low permeability to high molecular weight molecules.

The main function of the skin is precisely the regulation of the entrance of substances into the body. The skin of mammals consists of two main layers: the epidermis and the dermis. The epidermis is formed by the stratum corneum, stratum granulosum, stratum spinosum, and stratum basale, the stratum corneum constituting the surface of the skin and the stratum basale constituting the deepest part of the epidermis. The stratum corneum is the layer of skin which contributes the most to the barrier properties and which most obstructs the passage of cosmetically active substances to the deeper layers.

Various systems for traversing the stratum corneum and achieving penetration of cosmetic or therapeutic agents in deeper layers of the skin have been studied. One of these systems is the use of nanomaterials such as nanoparticles [Baron, B. J. Pharm. Sci., 2010, 99(1), 21-50]. Among proposed nanoparticles are lipid nanoparticles, polymer nanoparticles, magnetic nanoparticles, and metallic nanoparticles, among which are included gold nanoparticles [Gupta, R. and Rai, B.; J. Phys. Chem. B, 2016, 120(29), 7133-7142]. Said nanoparticles are described as being capable of penetrating deep layers of the skin (epidermis and dermis).

The possibility of using certain short peptides as compounds with anti-wrinkle activity has been known for some time. Examples of said peptides are acetyl hexapeptide-3, palmitoyl tetrapeptide-7, trifluoroacetyl-tripeptide-2, palmitoyl tripeptide-1, palmitoyl tripeptide-38, palmitoyl hexapeptide-14, and palmitoyl pentapeptide-4. Palmitoyl pentapeptide-4 (PP-4) is a peptide of formula Palm-L-Lys-L-Thr-L-Thr-L-Lys-L-Ser-OH (Palm-SEQ ID NO: 1). This peptide is also known by the name Matrixyl®. Said peptide and its anti-wrinkle activity have been described in WO 00/15188 A1.

WO 2008/079898 A1 discloses compositions that can comprise a colloidal metal, such as gold, which can be conjugated to a molecule, such as peptides, including Matrixyl®. However, WO 2008/079898 A1 does not disclose any specific composition comprising colloidal gold conjugated to Matrixyl®. This document is also silent about any advantage related to the use of Matrixyl® conjugated with a colloidal metal that would allow obtaining improved compositions for the treatment of wrinkles, in particular compositions having improved penetration of Matrixyl® in deep layers of the skin and improved stability of said peptide.

The objective of the present invention is to provide improved compositions for the treatment of the wrinkles.

SUMMARY OF THE INVENTION

The inventors have discovered that conjugating PP-4 peptide (a peptide of formula (I)) with gold nanoparticles achieves penetration of said peptide in deep layers of the skin. Said penetration is surprisingly much greater than that of the peptide of formula (I) in a composition of said peptide and gold nanoparticles without conjugation, as shown in the examples. Furthermore, the conjugation of the peptide of formula (I) with gold nanoparticles provides an unexpected stability to the peptide of formula (I), particularly against the enzymatic degradation by proteases. These effects are surprisingly not obtained when conjugating other peptides with gold nanoparticles, as shown in the examples. Therefore, one skilled in the art will not find any guideline whatsoever which will allow them to know which specific peptides can be conjugated with which nanoparticles for the purpose of obtaining formulations of said peptides with improved stability and good penetration.

Therefore in a first aspect, the present invention relates to gold nanoparticles conjugated with a peptide of formula (I):

R-L-Lys-L-Thr-L-Thr-L-Lys-L-Ser-OH (R-SEQ ID NO: 1)   (I)

wherein R is a $C_{10}$-$C_{22}$ acyl moiety, preferably a palmitoyl moiety.

In a second aspect, the present invention relates to a composition comprising the nanoparticles defined in the first aspect and water.

In a third aspect, the present invention relates to the use of nanoparticles as defined in the first aspect in the preparation of a composition as defined in the second aspect.

In a fourth aspect, the present invention relates to the (cosmetic) use of nanoparticles as defined in the first aspect or of a composition as defined in the second aspect for skin care.

In a fifth aspect, the present invention relates to a method for obtaining nanoparticles as defined in the first aspect, which comprises:
(a) reducing Au(III) from a compound containing said Au(III) to Au(0) by means of treatment with a reducing agent to form gold nanoparticles, and
(b) treating the gold nanoparticles obtained in step (a) with the peptide of formula (I).

DESCRIPTION OF THE DRAWINGS

FIG. 1 shows the percentage of cutaneous penetration of the different assayed compositions after 20 hours of incubation.

DETAILED DESCRIPTION OF THE INVENTION

Nanoparticles of the Invention

In a first aspect, the present invention relates to gold nanoparticles conjugated with a peptide of formula (I):

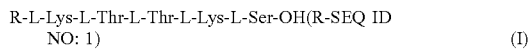

R-L-Lys-L-Thr-L-Thr-L-Lys-L-Ser-OH(R-SEQ ID NO: 1)    (I)

wherein R is a $C_{10}$-$C_{22}$ acyl moiety, preferably a palmitoyl moiety.

In the context of the present invention, the term "acyl" refers to a moiety having from 10 to 22 carbon atoms and having the structure R'—C(=O)—, wherein R' is a $C_9$-$C_{21}$ alkyl group. The number of carbon atoms of the acyl group corresponds to the number of carbon atoms of the alkyl substituent R' plus one carbon atom of the C(=O) group. Examples of acyl groups are $CH_3(CH_2)_{14}$—C(=O)— (i.e. palmitoyl), $CH_3(CH_2)_8$—C(=O)—, $CH_3(CH_2)_{10}$—C(=O)—, $CH_3(CH_2)_{12}$C(=O)—, $CH_3(CH_2)_{16}$—C(=O)—, $CH_3(CH_2)H$—C(=O)— and $CH_3(CH_2)_{20}$—C(=O)—, preferably palmitoyl.

The nanoparticles of the present invention have a gold core coated with the peptide of formula (I). In the context of the present invention, the term "conjugated" refers to the gold nanoparticles being bound to the peptide of formula (I) by means of an electrostatic ionic bond established between the negative charges of the gold surface of the nanoparticles and the positive charges of the amino acid Lys (lysine) present in the peptide of formula (I). The positive charge provided by this amino acid to the peptide is responsible for the bond established between the peptide of formula (I) and the gold surface of the nanoparticles, which results in the functionalization thereof where the peptide will coat the outer surface of the gold nanoparticles assuring the formation and stability thereof.

In the context of the present invention, the term "nanoparticle" refers to particles the mean diameter of which is less than 1000 nm, preferably less than 500 nm, more preferably less than 250 nm, more preferably less than 200 nm, more preferably between 1 and 1000 nm, more preferably between 1 and 500 nm, more preferably between 1 and 250 nm, more preferably between 1 and 200 nm, more preferably between 50 and 200 nm, more preferably between 100 and 200 nm, even more preferably between 150 and 200 nm.

The size of the nanoparticles can be determined by means of conventional methods in the art, particularly by means of dynamic light scattering (DLS). First the samples are prepared to determine particle size. To that end, 1 mg is weighed if it is powder and it is suspended in 1 mL of milli-Q $H_2O$. In the case of liquid samples, a 100 μL aliquot of the sample to which 900 μL of milli-Q $H_2O$ are added is collected with an automatic pipette. Then the particle size measurement is taken using quartz cuvettes and Zetasizer Nano ZS series equipment (Malvern Instruments) of the Instituto de Quimica Avanzada de Cataluña (Advanced Chemistry Institute of Catalonia), CSIC. Particle size measurements can be taken in triplicate for the purpose of demonstrating the reproducibility thereof.

In a preferred embodiment, the zeta potential of the nanoparticles of the invention is comprised between −5 mV and −60 mV, preferably between −10 mV and −50 mV, more preferably between −20 mV and −40 mV, even more preferably between −30 mV and −40 mV.

The term "zeta potential", "Z potential" or refers to a measurement of the surface charge of the nanoparticles. The zeta potential determines the degree of repulsion between adjacent nanoparticles having the same charge. If drops by more than a given value, the attractive forces exceed the repulsive forces and the nanoparticles cluster together.

The zeta potential of the nanoparticles can be determined by means of conventional methods in the art, particularly by means of the method described below.

The preparation of the samples for determining the Z potential consists of weighing 1 mg if it is powder and it is suspended in 1 mL of milli-Q $H_2O$. Whereas in the case of liquid samples, a 100 μL aliquot of the sample to which 900 μL of milli-Q $H_2O$ are added is collected with an automatic pipette. Then the Z potential measurement is taken using DTS1070 plastic cuvettes and Zetasizer Nano ZS series equipment (Malvern Instruments) of the Instituto de Quimica Avanzada de Cataluña (Advanced Chemistry Institute of Catalonia), CSIC. Z potential measurements can be taken in triplicate for the purpose of demonstrating the reproducibility thereof.

In a particular embodiment, the nanoparticles of the invention have a concentration of peptide of formula (I) from 0.01 to 1 mg per mg of nanoparticles, preferably from 0.01 to 0.5 mg/mg, more preferably from 0.05 to 0.5 mg/mg, more preferably from 0.1 to 0.5 mg/mg, even more preferably from 0.1 to 0.3 mg/mg.

Compositions of the Invention

In a second aspect, the present invention relates to a composition comprising the nanoparticles defined in the first inventive aspect and water.

In a particular embodiment, said composition is a dispersion of the nanoparticles in water, i.e., a colloid. In the context of the present invention a colloid refers to a system formed by two or more phases, a fluid (liquid) and another dispersed phase in the form of particles, the size of which is comprised between 1 and 1000 nm, and therefore, the particles are not visible at the macroscopic level but they are at the microscopic level.

In a particular embodiment, the dispersion of the nanoparticles in water, i.e., the colloid, has a concentration of peptide of formula (I) from 0.01 to 1 mg per ml of dispersion, preferably from 0.01 to 0.5 mg/ml, more preferably from 0.05 to 0.5 mg/ml, more preferably from 0.1 to 0.5 mg/ml, even more preferably from 0.1 to 0.3 mg/ml.

In a preferred embodiment, the composition contains at least 90% of water with respect to the sum of the weight of water and nanoparticles in the composition, preferably at least 95%, more preferably at least 99%, most preferably at least 99.5%.

In another preferred embodiment, the compositions of the invention may further comprise a cosmetic agent selected from the group consisting of surfactants, moisturizing agents, antioxidants, emollients, preservatives, humectants, viscosity modifiers, and a mixture thereof.

In the context of the present invention, a "surfactant" is a substance which decreases the surface tension of a composition with respect to the same composition in the absence of said component and furthermore facilitates the uniform distribution of the composition when it is used. Examples of surfactants suitable for the compositions of the invention are lauryl isoquinolinium bromide and isopropyl alcohol, polysorbate 20, steareth-2 (polyethylene glycol ether (2 units) and stearyl alcohol), oleth-2 (polyethylene glycol ether (2 units) and oleyl alcohol), PEG-8 caprylic/capric glycerides (ethoxylated with 8 units of polyethylene glycol), sodium cocoamphoacetate, coconut oil esters—polyglycerol 6, almond oil esters—PEG-8, ammonium cocosulfate and avocado oil esters PEG-11, and mixtures thereof.

In the context of the present invention, a "moisturizing agent" refers to a substance which increases the water content of the skin or hair and helps to keep it soft. Examples of moisturizing agents suitable for the compositions of the invention are *Vitis vinifera* seed oil, ceramide, glucosylceramide, grape oil esters—PEG-8, glyceryl esters—cocoa butter, shea butter cetyl esters, shea butter glyceride, lauryl cocoate, and mixtures thereof.

In the context of the present invention, an "antioxidant" refers to a substance which inhibits or reduces reactions promoted by oxygen, thereby preventing oxidation and rancidity. Examples of antioxidants suitable for the compositions of the invention are tocopherol, sodium tocopheryl phosphate, 3-glyceryl ascorbate, acetylcysteine, aloe vera plant extract, ascorbic acid, ascorbyl dipalmitate, ascorbic acid polypeptide, acetyl trihexylcitrate, ascorbyl linoleate, 2-acetylhydroquinone, apo-lactoferrin, ascorbyl glucoside, ascorbyl lactoside, and mixtures thereof.

In the context of the present invention, an "emollient" refers to a substance which softens the skin. Examples of emollients suitable for the compositions of the invention are apo-lactoferrin, *Acacia dealbata* flower wax, acetylarginine, acetylproline, acetylhydroxyproline, acetylated glycol stearate, algae extract, almond oil esters and propylene glycol, aminopropyltocopheryl phosphate, 1,2,6-hexanetriol, and mixtures thereof.

In the context of the present invention, a "preservative" refers to a substance which inhibits the development of microorganisms in the composition. Examples of preservatives suitable for the compositions of the invention are phenoxyethanol; a mixture of caprylyl glycol, glyceryl caprylate, glycerin, and phenylpropanol; a mixture of benzyl alcohol, glyceryl caprylate, and glyceryl undecylenate; a mixture of 2,2-hexanediol and caprylyl glycol; a mixture of phenethyl alcohol, and ethylhexylglycerin; a mixture of pentylene glycol, caprylyl glycol, and ethylhexylglycerin.

In the context of the present invention, a "humectant" refers to a substance which retains humidity. Examples of humectants suitable for the compositions of the invention are 3-glyceryl ascorbate, acetylcyclodextrin, propanediol, algae extract, 2,3-butanediol, 3-ethylhexylglyceryl ascorbate, 3-laurylglyceryl ascorbate, and capryl 3-glyceryl ascorbate.

In the context of the present invention, a "viscosity modifier" refers to a substance which increases the viscosity of a composition, preferably an aqueous composition. Examples of viscosity modifiers suitable for the compositions of the invention are carbomer, sodium carbomer, dextran sulfate sodium, carboxymethyl chitosan, propanediol, carboxymethyl dextran, steareth-30, steareth-40, steareth-50, sodium poly polynaphthalene sulfonate, croscarmellose, sodium glycereth-polyphosphate, and mixtures thereof.

In another preferred embodiment, the compositions of the invention are in the form of a cream, serum, emulsion, gel, foam, paste, ointment, milk, or solution, preferably in the form of cream, solution, serum or gel.

In a third aspect, the nanoparticles of the present invention are used in the preparation of a composition according to the present invention.

Said compositions can be prepared by means of mixing the nanoparticles of the invention with the rest of the components of the corresponding compositions.

Cosmetic Uses of the Nanoparticles and Compositions of the Invention

As explained in the description of the background of the present invention, palmitoyl pentapeptide-4 (PP-4, a peptide of formula (I)) presents anti-wrinkle activity [WO 00/15188 A1].

Therefore, in another aspect the present invention relates to the use of the nanoparticles or compositions of the invention in skin care. Said use is cosmetic.

In the context of the present invention, the term "care" refers to the maintenance or improvement of the qualities of the skin, such as wrinkles, elasticity, firmness, hydration, shine, tone, or texture, among others, preferably wrinkles.

In a preferred embodiment, skin care is the cosmetic treatment of wrinkles and/or cosmetic prevention of the onset of wrinkles.

In the context of the present invention, the term "treatment" refers to a non-therapeutic cosmetic treatment, in which the application of the composition of the invention on improves the cosmetic appearance of the skin in terms of wrinkles, by either reducing the depth of the wrinkles, reducing the number of wrinkles, or both.

In the context of the present invention, the term "prevention" refers to the capability of the composition of the invention to prevent, delay, or impede the onset of wrinkles in the skin.

Method of Obtaining the Nanoparticles of the Invention

In another aspect, the present invention relates to a method for obtaining nanoparticles of the invention, which comprises:
  (a) reducing Au(III) from a compound containing said Au(III) to Au(0) by means of treatment with a reducing agent to form gold nanoparticles, and
  (b) treating the gold nanoparticles obtained in step (a) with the peptide of formula (I).

The gold nanoparticles are formed in step (a).

In a particular embodiment, the reducing agent of step (a) is selected from the group consisting of sodium citrate, $NaBH_4$, $H_2O_2$, hydroxylamines (such as for example hydroxylamine sulfate, hydroxylamine-O-sulfonic acid, and hydroxylamine hydrochloride), tetrahydropyridines (such as for example, 1,3-bis(4-octadecyloxy-1,2,5,6-tetrahydropyridylmethyl)benzene), 1,3-bis(4-decyloxy-1,2,5,6-tetrahydropyridylmethyl)benzene) and 1,3-bis(4-methyl-1,2,5,6-tetrahydropyridylmethyl)benzene), oxalic acid, citric acid, and ascorbic acid; preferably the reducing agent is sodium citrate.

In another particular embodiment, the method of step (a) is carried out in a solvent selected from the group consisting of water, toluene, dichloromethane, acetonitrile, dimethylsulfoxide, dimethylformamide, acetone, ethanol, methanol, and mixtures thereof; preferably in water.

In a particular embodiment, the reduction reaction of step (a) is carried out at a temperature between 80° C. and 120° C., more preferably between 90° C. and 110° C., even more preferably between 95° C. and 105° C., most preferably at about 100° C.

In another particular embodiment, the compound of Au(III) which is reduced to Au(0) in step (a) is selected from the group consisting of gold (III) oxide ($Au_2O_3$), gold halides including $AuCl_3$ and $AuBr_3$, preferably the compound of Au(III) is $HAuCl_4$.

Once the gold nanoparticles have been obtained, step (b) of treatment with the peptide of formula (I) is performed. Preferably said treatment is performed by means of stirring a mixture, generally a dispersion, of the obtained gold nanoparticles and the peptide of formula (I). Said treatment is preferably performed by adding the peptide (I) to the reaction mixture of the gold nanoparticle formation.

Therefore in a particular embodiment, the method of step (b) is carried out in a solvent selected from the group consisting of water, toluene, dichloromethane, acetonitrile, dimethylsulfoxide, dimethylformamide, acetone, ethanol, methanol, and mixtures thereof, preferably in water.

Particularly, the treatment is performed by stirring at a temperature between 15° C. and 30° C., preferably between 20° C. and 25° C. Particularly, said stirring is maintained for 3 to 5 h, preferably for about 4 h.

The following non-limiting examples will additionally illustrate specific embodiments of the invention.

EXAMPLES

Examples 1-6. Synthesis and Characterization of Gold Nanoparticles and Peptide Compositions Materials and Methods Sodium citrate tribasic dihydrate and hydrogen tetrachloroaurate ($HAuCl_4$) from (Sigma Aldrich).

The UV-visible spectrum of the three samples of gold nanoparticles (GNP, GNP-P1, and GNP-P2) were determined in water using a UV-1800 Shimadzu spectrophotometer (Parc Cientific of Barcelona) and quartz cuvettes (Hellma Analytics). The UV-visible spectrum of each sample was determined in water at a concentration of 1 mg/mL.

The size of the nanoparticles (GNP, GNP-P1, and GNP-P2) was determined by dynamic light scattering (DLS) for which quartz cuvettes and Zetasizer Nano ZS series equipment (Malvern Instruments, Instituto de Quimica Avanzada de Cataluña) were used. The preparation of the samples consists of 1 mg if it is powder and it is suspended in 1 mL of milli-Q $H_2O$. In the case of liquid samples, a 100 µL aliquot of the sample to which 900 µL of milli-Q $H_2O$ are added is collected with an automatic pipette such that there is always a concentration of 1 mg/mL of sample. Then the particle size measurement is taken at a temperature of 25° C. The measurements were taken in triplicate for the purpose of demonstrating the reproducibility thereof.

The Z potential of the nanoparticles synthesized was determined using DTS1070 plastic cuvettes and Zetasizer Nano ZS series equipment (Malvern Instruments, of the Instituto de Quimica Avanzada de Cataluña, CSIC). The preparation of the samples consists of 1 mg if it is powder and it is suspended in 1 mL of milli-Q $H_2O$. In the case of liquid samples, a 100 µL aliquot of the sample to which 900 µL of milli-Q $H_2O$ are added is collected with an automatic pipette such that there is always a concentration of 1 mg/mL of sample. Then the Z potential measurement is taken at a temperature of 25° C. The measurements were taken in triplicate for the purpose of demonstrating the reproducibility thereof.

Examples 1-3: Synthesis of Nanoparticles GNP-P1, GNP-P2 and GNP

The gold nanoparticles (Examples 1-3) were synthesized using the Turkevich method based on the reduction of Au(III) to Au(0) using sodium citrate as reducing agent and the peptide of corresponding formula as stabilizing agent or in the absence of peptide:

Example 1: GNP-P1, wherein P1 is the peptide of formula (I) wherein R is a palmitoyl moiety (Palm-SEQ ID NO: 1);

Example 2: GNP-P2, wherein P2 is the peptide of formula (II) (P2; Palm-L-Cys-L-Lys-L-Thr-L-Thr-L-Lys-L-Ser-L-Cys-L-Thr-L-Thr-L-Lys-L-Ser-OH; Palm-SEQ ID NO: 2);

Example 3: GNP without peptide
where GNP refers to gold nanoparticles.

The gold nanoparticles (GNP, GNP-P1, and GNP-P2) were synthesized as follows:

5.76 mg of sodium citrate used as reducing agent was added to a 10 mL flask containing 3 mL of water. Then the solution was kept under reflux (100° C.) for 5 minutes. Then 0.6 mg of gold salt ($HAuCl_4$) were added until the formation of a dark red colored colloidal dispersion indicating that reduction of Au(III) to Au(0) has been completed which leads to obtaining gold nanoparticles that are stable over time called GNP. Once the sodium citrate-functionalized gold nanoparticles (GNPs) have been obtained, they were left to cool to room temperature and the peptide of formula (I) (P1) or the peptide of formula (II) (P2) was added in amounts of 1 and/or 3 mg. The dispersion was maintained under stirring for 4 h, thereby assuring suitable functionalization of the peptide of formula (I) or (II) on the gold surface, obtaining the gold nanoparticles called GNP-P1 and/or GNP-P2, respectively.

The concentration of the peptide (P1 or P2) incorporated in the nanoparticles (GNP-P1 and/or GNP-P2) was determined by HPLC, using a Waters 996 photodiode array detector instrument equipped with a Waters 2695 separation module and Millenium software. An Xbridge BEH130 C18 4.6×100 mm 3.5 µm reverse phase HPLC column by Waters was used. UV detection was performed at 220 nm, and a mobile phase B gradient of 5 to 100% was performed for 8 minutes at a flow rate of 1.0 ml/min. Under these conditions, the retention time being 6.4 min for both peptides P1 and P2. Mobile phase A: 0.045% of TFA/$H_2O$, mobile phase B: 0.036% of TFA/ACN.

Examples 4-5: Preparation of Peptide P1 and P2 Compositions

Compositions of the peptide of formula (I) (P1; Example 4) and of the peptide of formula (II) (P2; Example 5) were also prepared in the absence of nanoparticles by dissolving the corresponding peptide in water. 0.3 mg of the peptides of formula (I) (P1) and/or (II) (P2) were dissolved in 1 mL of water to have the same peptide concentration in the nanoparticles and in the absence thereof (0.3 mg/mL).

Example 6: Preparation of Peptide P1 Composition and Gold Nanoparticles without Conjugation Finally, a composition of the peptide of formula (I) and gold nanoparticles without conjugation (GNP+P1), example 6, was prepared.

A mixture of gold nanoparticles (GNPs) with the peptide of formula (I) (P1), without conjugation, both being at a concentration of 0.3 mg/mL of water, was prepared. The mixture was stirred for 5 minutes (GNP+P1) and was used immediately for performing the corresponding tests (degradation by proteases and pig skin penetration).

Characterization of Gold Nanoparticles

The nanoparticles were characterized by UV-visible absorption spectroscopy, DLS (Dynamic Light Scattering), and zeta potential.

Formation of the nanoparticles (GNP, GNP-P1, and GNP-P2) was confirmed by UV-visible spectroscopy, where the surface plasmon resonance (SPR) band characteristic of gold nanoparticles with a value between 510 and 526 nm was observed in all cases.

The results obtained for the synthesized nanoparticles are shown below in Table 1.

TABLE 1

| Example | | Nanoparticle diameter (nm) | Nanoparticle Zeta potential (mV) | Maximum concentration of peptide in nanoparticles (mg/mL) |
|---|---|---|---|---|
| 1 | GNP – P1 | 150-200 | −35 | 0.3 |
| 2 | GNP – P2 | 150-200 | −59 | 0.3 |
| 3 | GNP | 20-50 | −40 | — |

Example 7. Cutaneous Penetration

Materials and Methods

Cutaneous penetration was determined using Franz cells. The pig skin samples used in the experiments were cut into circles 3 cm in diameter. The pig skin was mounted on the receptor compartment of a Franz diffusion cell system with the stratum corneum facing up towards the donor compartment. 18 ml of phosphate-buffered saline (PBS) were used as receptor solution. An aliquot of the test samples (nanoparticles of Example 1 (GNP-P1), nanoparticles of Example 2 (GNP-P2), nanoparticles of Example 3 (GNP), formulation of peptide P1 of Example 4, formulation of peptide P2 of Example 5, mixture of nanoparticles and peptide P1 (GNP+P1) of Example 6 was applied on the pig skin. The Franz diffusion cells were mounted on an H+P Labortechnik Varimag Telesystem (Munich, Germany) and placed in a thermostatic bath (Haake).

Untreated skin control was also included. The Franz diffusion cells were kept at 32° C., and after 20 h of incubation, the receptor solution was analyzed by means of UV-visible absorption spectroscopy using a Shimadzu spectrophotometer UV-1800 (Parc Cientific of Barcelona) and quartz cuvettes (Hellma Analytics) to quantify the amount of gold nanoparticles present (GNP, GNP-P1, and GNP-P2). The amount of free peptide (P1, P2) was determined by means of HPLC, using a Waters 996 photodiode array detector instrument equipped with a Waters 2695 separation module and Millenium software. An Xbridge BEH130 C18 4.6×100 mm 3.5 μm reverse phase HPLC column by Waters was used. In both cases, UV detection was performed at 220 nm. Peptide P1 was analyzed with a mobile phase B gradient of 5 to 100% for 8 minutes at a flow rate of 1.0 ml/min, the retention time being 6.5 minutes. Peptide P2 was analyzed with a mobile phase B gradient of 0 to 20% for 8 minutes at a flow rate of 1.0 ml/min, the retention time being 1.5 minutes. The eluents used in both cases were: Mobile phase A: 0.045% of TFA/H$_2$O, mobile phase B: 0.036% of TFA/ACN.

Results

Penetration results after 20 h of incubation are shown in FIG. 1. As can be seen, there is a considerable increase in penetration upon conjugating the peptide of formula (I) with gold nanoparticles. However, said increase in penetration is not observed with the peptide of formula (II).

The results obtained after analysis of the receptor solutions showed that peptide (1) (Example 4; P1) only penetrated the outermost layers external of the skin, whereas in the case of skins treated with the gold nanoparticle (Example 1; GNP-P1), a high content of the peptide-conjugated nanoparticle was achieved, indicating that penetration reached more internal layers such as the epidermis and dermis.

Example 8. Peptide Degradation by Proteases

Materials and Methods 10 mg of each of the free peptides (P1, P2) were dissolved in 2 ml of phosphate-buffered saline (PBS) to yield a solution corresponding to a concentration of 5 mg/ml of peptide.

40 mg of each of the prepared nanoparticles GNP-P1, GNP+P1, and GNP-P2 with a 1% peptide content were dissolved in 1 ml of phosphate-buffered saline (PBS) to yield a final solution having a nanoparticles concentration of 40 mg/ml.

Papain (Fagon, Spain) was added (20 mg to the free peptide solutions or 1.5 mg to the nanoparticle solutions). The resulting solutions were incubated at 40° C. Samples were taken at study times (0 h, 0.33 h, 3 h and 24 h after the addition of papain), centrifuged at 1400 rpm for 1 min, and the supernatant was filtered using a 0.45 μm filter and analyzed by HPLC.

HPLC analysis was carried out in a Waters 996 photodiode array detector instrument equipped with a Waters 2695 separation module and Millenium software; an Xbridge BEH130 C18 4.6×100 mm 3.5 μm reverse phase column by Waters was used. UV detection was performed at 220 nm and a mobile phase B gradient of 5 to 100% was used for 8 minutes at 1.0 ml/min of flow. Under these conditions, the retention time of P1 is 6.4 min. Mobile phase A: 0.045% TFA/H$_2$O, mobile phase B: 0.036% TFA/acetonitrile.

Results

The obtained results are shown below in Table 2. As can be seen, the peptide of formula (I) conjugated with gold nanoparticles (GNP-P1) has an unexpected stability against the degradation with papain, whereas the peptide of formula (I) alone (P1) or in combination with gold nanoparticles but without conjugation (GNP+P1) rapidly degrades. Additionally, the peptide of formula (II) conjugated with gold nanoparticles (GNP-P2) also degrades rapidly by the action of papain.

TABLE 2

| | Stability (%) | | | | |
|---|---|---|---|---|---|
| Time (h) | P1 | P2 | GNP – P1 | GNP + P1 | GNP – P2 |
| 0 | 100 | 100 | 100 | 100 | 100 |
| 0.33 | 30 | 10 | 88 | 25 | 15 |
| 3 | 0 | 0 | 86 | 0 | 0 |
| 24 | 0 | 0 | 90 | 0 | 0 |

The invention claimed is:

1. Gold nanoparticles conjugated with a peptide of formula (I):

R-L-Lys-L-Thr-L-Thr-L-Lys-L-Ser-OH (R-SEQ ID NO: 1)  (I)

wherein R is a C14-C18 acyl moiety,
wherein the nanoparticles mean diameter is between 50 and 200 nm,
the nanoparticle exhibit a zeta potential between −5 mV and −60 mV, and
a concentration of the peptide of formula (I) is from 0.01 to 1 mg of peptide of formula (I) per mg of nanoparticles.

2. The nanoparticles according to claim 1, wherein the R moiety is a palmitoyl moiety.

3. A composition comprising the nanoparticles of claim 1 and water.

4. The composition according to claim 3, wherein the composition contains at least 95% (w/w) of water with respect to the sum of the weight of water and nanoparticles in the composition.

5. The composition according to claim 3, further comprising a cosmetic agent selected from the group consisting of surfactants, moisturizing agents, antioxidants, emollients, preservatives, humectants, viscosity modifiers, and mixtures thereof.

6. The composition according to claim 3, wherein the composition is in the form of a cream, serum, emulsion, gel, foam, paste, ointment, milk, or solution.

7. A method for the preparation of a composition comprising the nanoparticles of claim 1, comprising mixing the nanoparticles as defined in claim 1 and water.

8. A method of using the nanoparticles according to claim 1 or a composition comprising the nanoparticles according to claim 1, comprising applying to the skin the nanoparticles according to claim 1 or the composition comprising the nanoparticles according to claim 1 for skin care.

9. The method according to claim 8, wherein the skin care is the cosmetic treatment of wrinkles and/or cosmetic prevention of the onset of wrinkles.

10. A method for obtaining the nanoparticles as defined in claim 1, comprising:
(a) reducing Au(III) from a compound containing said Au(III) to Au(0) by means of treatment with a reducing agent to form gold nanoparticles, and
(b) treating the gold nanoparticles obtained in step (a) with the peptide of formula (I).

11. The method according to claim 10, wherein the reducing agent of step (a) is sodium citrate.

12. The method according to claim 10, wherein steps (a) and (b) are carried out in water.

13. The method according to claim 10, wherein the compound of Au(III) of step (a) is $HAuCl_4$.

* * * * *

SEQUENCE LISTING

```
Sequence total quantity: 2
SEQ ID NO: 1              moltype = AA   length = 5
FEATURE                   Location/Qualifiers
source                    1..5
                          mol_type = protein
                          organism = synthetic construct
SEQUENCE: 1
KTTKS                                                                      5

SEQ ID NO: 2              moltype = AA   length = 11
FEATURE                   Location/Qualifiers
source                    1..11
                          mol_type = protein
                          organism = synthetic construct
SEQUENCE: 2
CKTTKSCTTK S                                                              11
```